(12) United States Patent
Stewart

(10) Patent No.: US 10,905,521 B2
(45) Date of Patent: Feb. 2, 2021

(54) SYSTEM, APPARATUS AND METHODS FOR RECOGNIZING SURGICAL ARTICLES LEFT INSIDE PATIENTS

(71) Applicant: Innovo Ventures, LLC, Ladera Ranch, CA (US)

(72) Inventor: Brian E. Stewart, Ladera Ranch, CA (US)

(73) Assignee: Innovo Ventures, LLC, Ladera Ranch, CA (US)

( * ) Notice: Subject to any disclaimer, the term of this patent is extended or adjusted under 35 U.S.C. 154(b) by 0 days.

(21) Appl. No.: 16/000,667

(22) Filed: Jun. 5, 2018

(65) Prior Publication Data

US 2018/0344429 A1    Dec. 6, 2018

Related U.S. Application Data

(60) Provisional application No. 62/515,856, filed on Jun. 6, 2017.

(51) Int. Cl.
*A61B 90/90*    (2016.01)
*A61B 90/00*    (2016.01)
(Continued)

(52) U.S. Cl.
CPC ............. *A61B 90/90* (2016.02); *A61B 90/36* (2016.02); *A61F 13/36* (2013.01); *A61F 13/44* (2013.01); *A61B 90/39* (2016.02); *A61B 2090/376* (2016.02); *A61B 2090/3966* (2016.02); *G06T 2207/10121* (2013.01)

(58) Field of Classification Search
CPC . A61F 13/44; A61B 90/39; A61B 2090/3937; A61L 31/18
See application file for complete search history.

(56) References Cited

U.S. PATENT DOCUMENTS 3,965,907 A     6/1976  Hardy et al.
4,205,680 A  *  6/1980  Marshall ................. A61F 13/44
                                                   604/362
(Continued)

FOREIGN PATENT DOCUMENTS

WO    WO-2016118749 A1    7/2016
WO    WO-2018226860 A1    12/2018

OTHER PUBLICATIONS

"International Search Report for PCTUS2018036305 dated Sep. 21, 2018".
(Continued)

*Primary Examiner* — Hongmin Fan
(74) *Attorney, Agent, or Firm* — Wilson Sonsini Goodrich & Rosati

(57) ABSTRACT

System, methods and apparatus related to surgical articles used during surgery. The system, methods and apparatus may include features such as an element/substrate added to surgical articles which enables the recognition by human visualization of the surgical articles when left inside patient bodies when viewed with medical imaging technologies. The element/substrate may include a plurality of three dimensional objects. Alternatively, the element/substrate may comprise a ribbon of radiopaque material having cut-puts or other radiolucent regions which provide image artifacts observable under fluoroscopic imaging.

12 Claims, 9 Drawing Sheets

(51) Int. Cl.
*A61F 13/36* (2006.01)
*A61F 13/44* (2006.01)

(56) References Cited

U.S. PATENT DOCUMENTS

| | | | |
|---|---|---|---|
| 4,244,369 A | | 1/1981 | McAvinn et al. |
| 5,041,103 A | * | 8/1991 | Rupinskas ............... A61F 13/44 |
| | | | 602/900 |
| 5,045,080 A | * | 9/1991 | Dyer ....................... A61L 15/18 |
| | | | 604/362 |
| 5,112,325 A | | 5/1992 | Zachry |
| 5,254,200 A | * | 10/1993 | Takagi ................ B29C 63/0013 |
| | | | 156/249 |
| 5,575,781 A | | 11/1996 | DeBusk |
| 5,664,582 A | * | 9/1997 | Szymaitis ................ A61B 5/06 |
| | | | 128/897 |
| 5,792,128 A | * | 8/1998 | DeBusk .................. A61F 13/44 |
| | | | 604/362 |
| 6,777,623 B2 | | 8/2004 | Ballard |
| 7,001,366 B2 | | 2/2006 | Ballard |
| 7,465,847 B2 | | 12/2008 | Fabian |
| 2005/0049563 A1 | * | 3/2005 | Fabian ..................... A61F 13/44 |
| | | | 604/362 |
| 2007/0219516 A1 | * | 9/2007 | Patel ....................... A61F 13/36 |
| | | | 604/362 |
| 2015/0245955 A1 | | 9/2015 | Choudhury et al. |
| 2018/0000556 A1 | * | 1/2018 | Blair ....................... G06K 19/02 |

OTHER PUBLICATIONS

Robert; Crima et al., "Incidence and Characteristics of Potential and Actual Retained Foreign Object Events in Surgical Patients", the American College of Surgeons, Jul. 2008, vol. 207, No. 1, 80-87.
Stanislaw; Pa Stawicki et al., "Retained Surgical Items: A Problem Yet to be Solved", the American College of Surgeons, 2013, vol. 216, No. 1, 15-22.

* cited by examiner

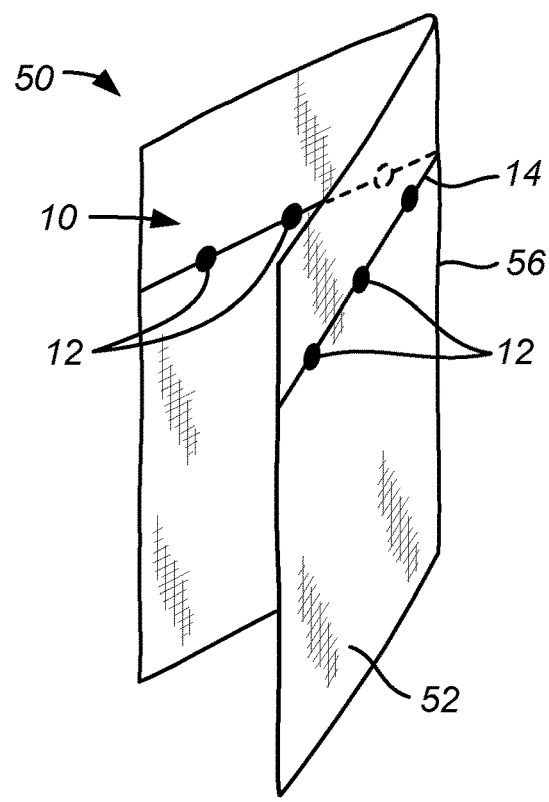
FIG. 5
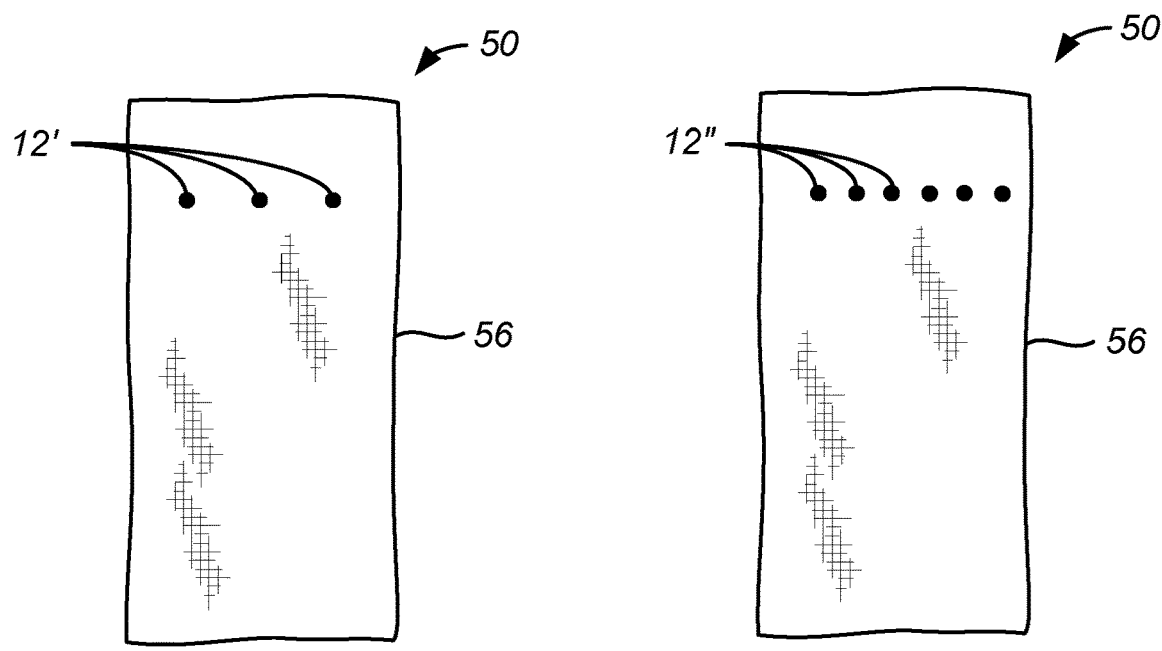
FIG. 6A   FIG. 6B

SYSTEM, APPARATUS AND METHODS FOR RECOGNIZING SURGICAL ARTICLES LEFT INSIDE PATIENTS

CROSS-REFERENCE TO RELATED APPLICATION

This application claims the benefit of provisional application No. 62/515,856, filed on Jun. 6, 2017, the full disclosure of which is incorporated herein by reference.

BACKGROUND OF THE INVENTION

1. Field of the Invention

The present invention relates generally to surgical articles used during surgery. More particularly, the present invention relates to the recognition of surgical articles located inside a patient's body by human visualization of medical imagining technologies.

During a surgical procedure it is generally necessary for surgical articles to be placed into or around the patient's surgical incision site. Such articles may include surgical instruments, towels, sponges and the like. Before, during and after surgical procedures surgical teams go to great efforts to account for all the surgical articles used during that surgery in an attempt to avoid one or more of those items being inadvertently left inside a patient. Patient morbidity associated with unintentionally retained surgical articles can range from infection to mortality and the financial implications can be substantial.

Due to a number of factors surgical articles made of fabric or fabric like materials, such as surgical sponges and towels, prove particularly difficult to account for during and after surgery. Accordingly, these types of surgical articles account for the majority of items inadvertently left inside patients. Surgical sponges and towels are commonly used during surgical procedures to absorb body fluids, mostly blood, of the patient both inside the incision and around the surgical site. These surgical items are usually made of flexible, absorbent fabric or fabric like material such as cotton and are often intentionally or unintentionally folded one or more times during use. Additionally, when saturated with blood these items alter in size and shape and therefore become hard to distinguish from body tissue and each other.

In an effort to avoid unintentionally leaving surgical articles inside patients after surgery, surgical teams routinely count all the individual items before and after each surgery. If the count of these items taken after a surgical procedure does not match the count prior to that procedure, efforts are made to find the missing item or items until the counts match. Additionally, surgical articles intended to be placed inside the patient or around the surgical incision commonly include an x-ray detectable element. In the event one or more surgical articles cannot be accounted for, x-ray technology is commonly utilized in an effort to aid surgical teams in finding the missing item or items or to conclude the missing item or items are not inside the patient.

Increasingly, additional technologies including barcoding, radio frequency and radio frequency identification are being utilized by surgical teams to assist them in counting and accounting for surgical articles, however it is still common and desirable for these solutions to further incorporate x-ray detectable elements in their articles in an effort to provide a confirmatory or backup methodology for locating a lost item or items and confirming no items are inside a patient.

Surgical articles made of fabric or fabric like materials, such as surgical sponges and towels, commonly include an elongated radiopaque thread like element designed to be recognized when viewed with x-ray fluoroscopy. Despite the presence of thread like radiopaque elements, surgical articles made of fabric or fabric like materials, such as surgical sponges and towels, are commonly missed by individuals trained to recognize such items with medical imaging technologies and inadvertently left inside patients. In a study entitled "Incidence and Characteristics of Potential and Actual Retained Foreign Object Events in Surgical Patients" (Cima et al, *Incidence and Characteristics of Potential and Actual Retained Foreign Object Events in Surgical Patients*, Journal of the American College of Surgeons, December 2007, pages 80-87), in 33% of patients where intra-operative x-rays were utilized the retained surgical article was mistakenly not recognized. In another study entitled "Retained Surgical Items: An Problem Yet to be Solved" (Stawicki et al, *Retained Surgical Items: A Problem Yet to Be Solved*, Journal of the American College of Surgeons, August 2012, pages 15-22) in 48% of retained sponge cases the sponges were missed on initial x-ray interpretation.

There are a multitude of reasons a thread like element attached to surgical articles made of fabric or fabric like material such as a surgical sponge or towel intended to be recognized with human visualization on medical imaging technologies can be missed. One reason may be that the article and element was folded one or more times making the x-ray element more difficult to see. Another reason may be that the x-ray thread element is mistakenly thought to be a wire or wire like item, as wires and wire like items are often placed in and around a patient at the time an x-ray may be taken. Examples include wires and wire like items from devices intentionally left inside patients including pain management devices, defibrillators and pacemakers as well as tubes or wires from items placed on top of the patient post-operatively such as IVs, and wires from various life support and patient monitoring devices. Another reason may be the image taken of the article is captured at an angle such that the 2 dimensional nature of the thread like x-ray element is more difficult to see or appears similar to another object. Another reason may be that the image taken of the article is taken at a particular cross section of the thread like element such that the 2 dimensional nature of the thread like element does not appear to be a thread like element. This may be particularly an issue when newer or more advanced imaging technologies are utilized that are capable of taking an image of a specific depth or cross section of the patient as opposed to an image of the patient in their entirety. Such imaging technologies may include magnetic resonance imaging or ultrasound imaging. Another reason that a thread like x-ray element may be missed is that when an x-ray is taken of a moving patient, such as when the target area is the abdomen and the patient is breathing, an x-ray element will sometimes appear blurred or smeared and thus may be misinterpreted as something other than a thread like x-ray element.

For these reasons it would be desirable to provide alternative and improved systems, methods and apparatus for the recognition of surgical articles left inside of patients. In particular, it would be desirable to provide alternative systems, methods and apparatus for improving the ability to recognize surgical articles left inside of patients using human visualization of those items with medical imaging technologies, including both x-ray and other imaging technologies.

2. Background of the Prior Art

U.S. Pat. No. 7,465,847 discloses the use of spherical radiopaque markers to aid in the visual recognition of surgical sponges, however there are considerable differences between the invention disclosed in the '847 patent and the present invention and the present invention affords significant advantages over the product disclosed in the '847 patent. The product disclosed in the '847 patent utilizes a predetermined number of specifically three spherical markers on each surgical sponge and those three spherical radiopaque markers are closely grouped, proximate and directly contiguous to one another. The present invention utilizes a plurality of three dimensional objects, including potentially spherical shapes, however unlike the '847 patent the present invention utilizes a plurality of three dimensional shapes in a fashion wherein those objects are intentionally not closely grouped, proximate nor directly contiguous to one another. Further unlike the '847 patent, the present invention utilizes a plurality of three dimensional objects, the exact number of which on each article/sponge is not predetermined. Further, the plurality of objects of the present invention are tethered together with a flexible material that intentionally creates spaces between each object, hence they are not closely grouped together, are not proximate to each other and not directly contiguous to one another. Further, the present invention includes those connected/tethered objects and the connecting material throughout the entire length of at least one side of the surgical article. Advantages of the approach of the present invention as compared to the '847 patent include: (1) because the substrate runs at least the entire length of at least one side of the article, substantially more three dimensional objects can be included in each article, increasing the probability of recognition by human visualization on medical imaging, (2) because the plurality of three dimensional objects are not proximate nor directly contiguous to one another and are instead spaced out and tethered with a flexible material, the resulting substrate allows for the inclusion of those objects along at least one side of the article without compromising the clinically desired flexible nature of the fabric or fabric like material of the surgical article, (3) because the plurality of three dimensional objects are spaced out and connected with a flexible material, that flexible tethering/connecting material can be used not just to tether/connect the objects but also to adhere the objects to the fabric or fabric like material of the surgical article in an effective and cost effective manner. This can be done by utilizing a flexible tethering/connecting material that either binds to the fabric or fabric like material through the application of heat and pressure (being melted and pressed into the fabric or fabric like material) or by sewing the tethering/connecting material to the fabric/fabric like material.

U.S. Pat. Nos. 6,777,623 and 7,001,366 (a continuation of the '623 patent) disclose the use of radiopaque objects to count and account of surgical sponges, however there are considerable differences between the two inventions disclosed in the '623 and '366 patents and the present invention and the present invention affords significant advantages over the product disclosed in the '623 and '366 patents. The product disclosed in the '623 and '366 patents utilizes exactly one radiographically detectable object affixed to each individual surgical article and depends on this approach to obtain an accurate count of each article. Further, a separate scanning device is utilized that can detect and count a large number of the objects, one on each sponge, within a container. Unlike the '623 and '366 patent, the present invention utilizes a plurality of three dimensional objects tethered together and included with each individual surgical article and further that those connected/tethered objects run at least the length of one side of the surgical article. Additionally, the plurality of objects included with each surgical article in the present invention are adapted to be recognized by human visualization when viewed with medical imaging technology whereas the '623 patent specifically describes the use of a scanning device coupled with a counting device utilizing non-human means for counting each sole object on each surgical sponge. Advantages of the present invention as compared to the '623 and '366 patent include: (1) because the '623 and '366 patent utilizes a non-human counting mechanism and a scanning device and a container the invention is considerably more expensive to implement than the present invention, (2) unlike the '623 and '366 patent invention which utilizes exactly one radiopaque object on each surgical article, the present invention includes a plurality of three dimensional objects designed to be recognized by human visualization, as such the probability of the human recognition of said objects when viewed on medical imaging technologies is higher, (3) the '623 and '366 patents disclose that by using the invention as described "a surgical team can insure that no surgical sponge is left in a patient without performing the messy and time-consuming job of individually counting sponges as they are entered and disposed of from the surgical site", whereas the current invention makes no attempt to replace the manual counting process of these items; doing so creates a sole dependency on every facet of the technology to perform correctly, and for there not to be any human user error in any step in the process, and thus opens up the safety of the patient to incremental technology and user error risk.

US2015245955 describes surgical gloves having RO markers which are "readily recognizable and differentiated from the images produced by other items and structures commonly seen in x-rays."

U.S. Pat. No. 7,465,847 shows individual stars, diamonds or other RO patterns which are individually attached to a sponge. In FIG. 4, a diamond-shaped marker 18 is mounted on what appears to be an RFID tag 20.

U.S. Pat. No. 7,001,366 shows a surgical sponge having RO beads on a patch but does not show an elongate ribbon (it does use the word tape at col. 5, line 57) and not multiple beads or other objects on a single patch.

U.S. Pat. No. 4,244,369 shows a surgical sponge having a thermoplastic "elongated ribbon" which is stitched to a sponge. The ribbon does not define distinct image artifacts.

U.S. Pat. No. 3,965,907 shows an RO polymer which is patterned in situ on a sponge to have a unique thickness/width pattern to enhance recognition. It is not pre-formed and does not have individual stars or other shapes formed by RO/radiolucent regions.

SUMMARY OF THE INVENTION

The present invention provides apparatus, systems and methods for improved recognition of surgical articles left inside patients. A plurality of three dimensional objects contain material making them more easily recognized with human visualization when using medical imaging technologies are included in each surgical article. Such imaging technologies may include x-ray, ultrasound or magnetic resonance imaging. Such material may include barium sulfate ($BaSO_4$). In another embodiment, the three dimensional objects will be comprised entirely of materials making them more easily recognized with human visualization when using medical imaging technologies. Such materials may include steel, titanium or another alloy. The three dimensional objects may be shaped such that they appear in substantially the same shape when viewed at various angles and at various cross sections. Such shapes may spherical.

In one embodiment the plurality of three dimensional objects are tethered or otherwise connected together with a flexible material. As used herein, the term "tethered" will means that the three dimensional objects will be connected by some form of a flexible, elongate member, typically a filament, fiber, thread, suture, wire, or similar string-like element where the individual three dimensional objects are formed integrally with, strung over, or otherwise coupled to the flexible elongate member. Alternatively, three dimensional objects may be tethered together in a sleeve or other tubular structure. The three dimensional objects may be tethered together by: (i) the same material comprising the objects, (ii) through another material or (iii) by those objects being included in or on a substrate. Usually, the material connecting the three dimensional objects will contain a material that enable those objects to be recognized on medical imaging technologies through human visualization. Such material may include barium sulfate ($BaSO_4$).

In one embodiment one of the plurality of tethered/ physically connected three dimensional objects is spaced from another in a substantially similar distance. In another embodiment two or more three dimensional objects clustered together in relatively close proximity to each other are spaced out from another group of two or more three dimensional objects clustered together in relatively close proximity to each other in a substantially similar distance.

In one embodiment one of the plurality of three dimensional objects on/in a substrate is spaced from another on or in a substrate in a substantially similar distance. In another embodiment two or more three dimensional objects clustered together in relatively close proximity to each other on/in a substrate are spaced out from another group of two or more three dimensional objects clustered together in relatively close proximity to each other in a substantially similar distance on/in the substrate.

In one embodiment, the plurality of tethered three dimensional objects are attached to a surgical article comprised of fabric or fabric like material across the substantially the entire length of one or more sides. In exemplary embodiments the tethered three dimensional objects are attached to a single layer of continuous fabric or fabric like material in a continuous manner, then the fabric or fabric like material may be then be cut into individual pieces then further may be folded one or more times. In exemplary embodiments the material connecting the tethered three dimensional objects can be of a material that at least partially melts when heat is applied such that the connecting material melts to adhere to the fabric or fabric like material. Such material may be at least partially composed of a heat-meltable polymer. In another embodiment the material connecting the tethered three dimensional objects may be sewn directly to the fabric or fabric like material.

In another embodiment the substrate with the objects on or in it is attached substantially the entire length of one or more sides of a surgical article comprised of fabric or fabric like material. In exemplary embodiments the substrate is attached to a single layer of continuous fabric or fabric like material in a continuous manner then the fabric or fabric like material may be then cut into individual articles then further may be folded one or more times. In exemplary embodiments the substrate can be at least partially of a material that at least partially melts when heat is applied such that the substrate melts to adhere to the fabric or fabric like material. Such material may be at least partially composed of a heat-meltable polymer. In another embodiment the substrate may be sewn directly to the fabric or fabric like material.

In one embodiment the surgical articles may be made of fabric or fabric like material, the color of the absorbent material being one that, when soaked with blood contrasts with the color of blood. Such color may be blue or green.

In a first particular aspect of the present invention, a surgical article comprises a sheet of an absorbent fabric material configured to absorb body fluid. A first plurality of discrete radiopaque elements are distributed over at least one distribution line of extending from one edge of the sheet to another edge of the sheet, where the first plurality of discrete radiopaque elements are arranged in a tethered construct which is attached to the sheet of the absorbent fabric material.

The tethered construct typically comprises a flexible elongate member where the plurality of discrete radiopaque elements are formed integrally with or secured to the flexible elongate member. For example, the flexible elongate member can be a filament, fiber, thread, suture, wire, or similar string-like element where the individual radiopaque elements are strung over the flexible elongate member. In such constructs, the filament, fiber, thread, suture, wire, like, will usually be formed separately from the discrete radiopaque elements, and the radiopaque elements will be attached over the elongate member using adhesives, by crimping, by applying a combination of heat and pressure or by other conventional techniques.

Alternatively, the tethered construct may be molded to form both the plurality of discrete radiopaque elements and the flexible elongate member into a single integrated or "monolithic" unit. In such cases, the elongate member and the radiopaque elements will typically be formed from the same material although the amount of a radiopaque filler could vary with the radiopaque elements typically having a higher radiopacity. Forming the entire tethered construct in a single fabrication process will often be an efficient and preferred manufacturing approach.

In other embodiments, the flexible elongate member may comprise a sleeve or other tubular member where the plurality of the discrete radiopaque elements are secured within an inner lumen or passage of the tubular member. For example, tubular member may be a sock-like member with the radiopaque elements distributed within the interior of the sock. Usually, the radiopaque elements will be secured so that they are not able to move within the interior of the tubular member. For example, they can be glued, sutured, welded, or otherwise secured in place.

The tethered constructs will be attached to the sheet of absorbent fabric material by any one of a variety of techniques. For example, the tethered construct may be woven into the fabric, sutured to the fabric, welded to the fabric, heat sealed to the fabric, laminated to the fabric, or the like.

In the exemplary embodiments, the sheet of absorbent material is configured to be folded so that individual ones of the discrete radiopaque elements on one side of the fold will align in some desired pattern with others of the discrete radiopaque elements on the other side of the fold to enhance a radiopaque image artifact when the sheet is viewed under fluoroscopy or X-ray in its folded configuration. For example, the sheet may be configured to be folded into two halves along a fold line where the distribution line of the radiopaque elements crosses over the fold line so that some of the plurality of the discrete radiopaque elements are on one side of the fold line and others of the plurality of discrete radiopaque elements are on the other side of the fold line. In this way, when the sheet of absorbent material is folded, radiopaque elements on opposite sides of the fold line may stack over each other in order to reinforce the radiopaque image artifact when the image is scanned under fluoroscopy or x-rays. Alternatively, the discrete radiopaque elements on one side of the fold line may be interspersed between others of the discrete radiopaque elements on the other side of the fold line after folding. In this way, the linear density of the radiopaque elements is increased. In still other embodiments, at least one distribution line is oriented at an acute angle relative to the fold line so that the discrete elements on one side of the fold line and those on the other side of the fold line are oriented in a V-shape relative to each other after the sheet is folded. In still other embodiments, the sheets may include two, three, four, or even more distribution lines for the radiopaque elements.

In a second particular aspect of the present invention, a surgical article comprises a sheet of an absorbent fabric material configured to be folded and to absorb body fluid in the folded configuration. A first plurality of discreet radiopaque elements is distributed over at least one distribution line extending from one edge of the sheet to another edge of the sheet. Individual ones of the discrete radiopaque elements will align with others of the discrete radiopaque to enhance a radiopaque image artifact when the sheet is in its folded configuration.

The absorbent fabric material may be any type of surgical absorbent material, typically being a woven surgical sponge material. The two halves of the sheet are typically folded at least once over a fold line where the at least one distribution line crosses over the fold line so that some of the plurality of discrete radiopaque elements will be on one side of the fold line and others will be on the other side of the fold line after the article is folded. The fold line will typically be disposed along a center or other line of symmetry of the absorbent material but could in other instances be located asymmetrically. Also, note that the absorbent material may have more than one fold line so that the article may be first folded along one fold line followed by folding along a secondary fold line and optionally further fold lines.

The locations of the discrete radiopaque elements over the sheet of absorbent fabric material may be specifically chosen so that the radiopaque image artifact provided by the radiopaque elements is in some way enhanced after the sheet of material is folded one or more times. For example, the radiopaque elements on one side of a fold line may stack over or near others of the radiopaque elements on the other side of the fold line after folding. Alternatively or additionally, the radiopaque elements on one side of the fold line may be interspersed between others of the radiopaque elements on the other side of the fold line after the absorbent fabric sheet is folded. Many other patterns are also available. For example, at least one distribution line may be oriented at an acute angle relative to the fold line so that the discrete radiopaque elements on one side of the fold line and the discrete radiopaque elements on the other side of the fold line are oriented in a V-shape relative to each other after the sheet is folded.

The plurality of discrete radiopaque elements will typically be arranged in a tethered construct where the tethered construct is attached to the sheet of absorbent fabric material. A number of different embodiments for such tethered constructs have been described above.

In alternative embodiments, the invention utilizes a ribbon or other elongated substrate affixed to a surgical sponge, that substrate containing radiopaque material, that substrate being shaped and applied to the surgical sponge material in a fashion so as to improve the human visual recognition of said substrate (and hence the surgical sponge to which it is affixed) when viewed on medical imaging technologies (with a primary focus on x-ray). The substrate will be designed and shaped so as to: (1) provide meaningful visual contrast intended to "catch the eye" of those viewing the substrate on x-ray (as the shape will be designed not to look like any other object typically used in or around a patient in surgery), and (2) include distinct shaping used ubiquitously with the invention to help identify the object as a surgical sponge (for example the ubiquitous use of a star shape). The radiopaque material used may be a material providing a higher radio-opacity (hence a brighter contrast under x-ray) than barium sulfate, the material traditionally used with surgical sponges.

In such alternative embodiments, the substrate will likely be affixed to the sponge material either through sewing or through a heat press process using a combination of heat, pressure and dwell time in order to melt the substrate (or the layer contacting the sponge material) onto the sponge material. The substrate will likely be affixed to the sponge material either continuously to the sponge material (with the sponge material then being cut and converted into a final sponge as a secondary step) or as a discrete segment, i.e. a length or amount of substrate applied to each sponge after formation of the sponge.

For example, any ribbon or other elongated substrates material may be applied in a continuous fashion and affixed with a heat press process, e.g., the sponge material and the substrate may be placed through heated rollers in a continuous fashion which applies the heat and pressure to affix the substrate to the sponge material. If a discrete segment, length, or amount may be affixed with a heat press process, e.g. a pre-cut segment of substrate may be placed in a desired attachment position on sponge material then a heat press applied directly over the substrate.

BRIEF DESCRIPTION OF THE DRAWINGS

FIG. 5 illustrates the surgical article of FIG. 4 partially folded along a fold line to bring the discrete radiopaque elements into alignment after folding.

FIG. 6A illustrates a first exemplary of distribution of discrete radiopaque elements on the folded article of FIGS. 4 and 5.

FIG. 6B illustrates a second exemplary embodiment of a distribution of discrete radiopaque elements on the folded surgical article of FIGS. 4 and 5.

DETAILED DESCRIPTION OF THE INVENTION

Figure 1A:
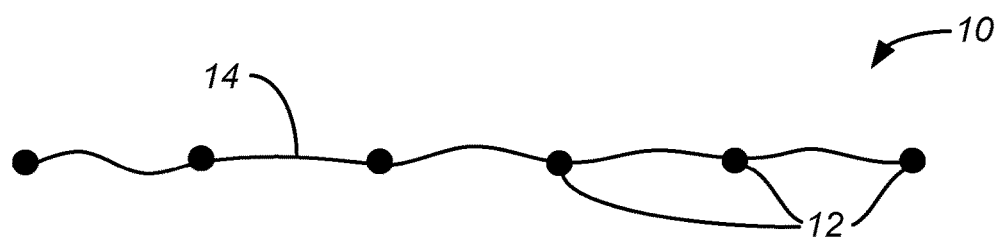
FIGS. 1A-1C illustrate the radiopaque elements of the present invention arranged in tethered constructs in different patterns, where the radiopaque elements are secured over a flexible elongate member.

Referring to FIG. 1A, a first embodiment of a tethered construct 10 includes a first plurality of radiopaque elements 12 distributed along the length of a filament 14. As used herein, the word "discrete" means that each radiopaque element exists as a unitary component having any of the dimensions and formed from any of the materials described elsewhere herein. Typically, the radiopaque elements 12 will be small spheres having a diameter in the range from approximately one (1) millimeter to seven (7) millimeters, preferable from approximately one and a half (1.5) millimeters to four (4) millimeters. When secured over a filament 14, as illustrated in FIG. 1A, the radiopaque elements may have small holes or passages allowing the filament to be threaded through the element. Alternatively, the radiopaque elements may be integrally formed with the filament by molding, extrusion, or other fabrication technique to form the tethered construct. Once each element is properly positioned on the filament, typically with a spacing in the range from five (5) millimeters to ten 100 millimeters, usually from ten (10) millimeters to 25 millimeters, the elements will be fixed in place, e.g. by gluing, crimping, heat welding, or the like.

Figure 1B:
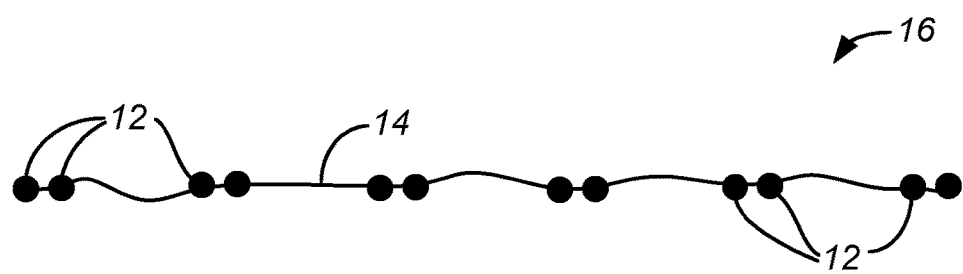
Figure 1C:
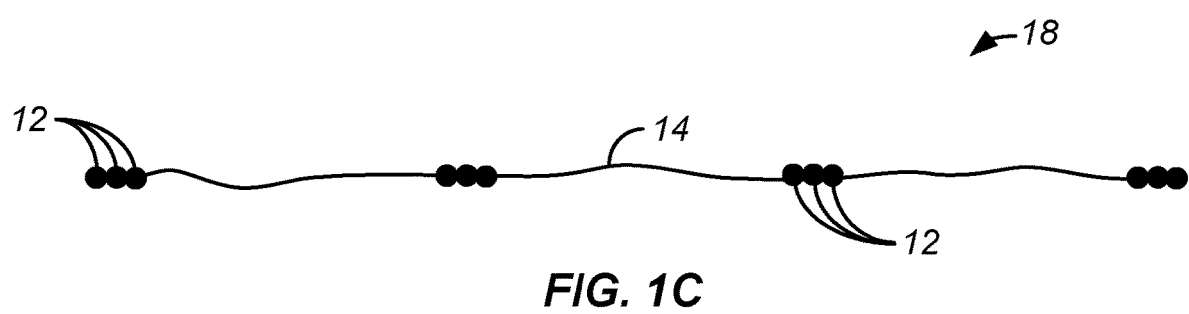

While the first embodiment of the tethered construct 10, as shown in FIG. 1A, has single radiopaque elements distributed evenly along its length, the distribution pattern and spacing of radiopaque elements along a filament 14 may vary widely. For example, as show in FIG. 1B, a second embodiment of a covered construct 16 may have pairs of radiopaque elements 12 distributed along the length of a filament 14. When using pairs of radiopaque element 12, the individual elements may be slightly smaller than when using single radiopaque elements 12. Similarly, in the third embodiment of a tethered construct 18 as show in FIG. 1C, the radiopaque elements 12 may be arranged in triplets, in which case fewer of the triplets or clusters of the elements may be needed. That is, in each of the embodiments of FIGS. 1A and 1B, there are six individual or clustered elements, in the tethered construct 18 of FIG. 1C, there are only four total clusters on the filament 14. It will be appreciated, of course, that the total number of individual radiopaque elements 12 or clusters of elements may vary widely with anywhere from 3 to 24, often from 4 to 10. Also, with regard to the embodiments of FIGS. 1A-1C, the filament 14 may be any of the elongate, flexible tethers referred to above, including fibers, threads, sutures, wires, and the like.

In each of the tethered constructs 10, 16 and 18 above, the radiopaque elements 12 are formed separately from the filament. In other embodiments, the radiopaque elements and filaments may be formed from the same material, typically a polymer loaded with a radiopaque filler. The tethered constructs may then be formed using convention polymer processing techniques, such as molding or extrusion.

Figure 2A:
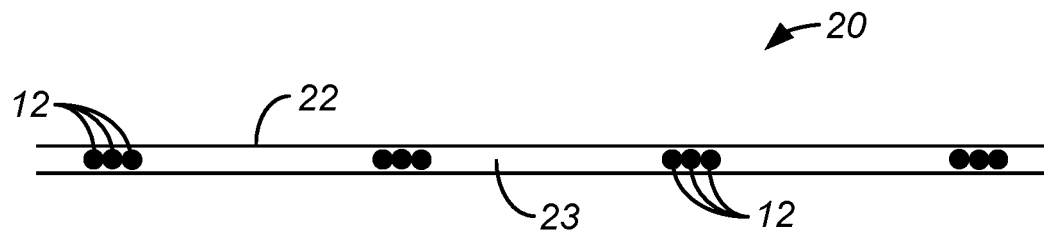
FIGS. 2A-2C illustrate embodiments of the present invention where the radiopaque elements are secured inside of tubular flexible elongate members in order to form tethered constructs.
Figure 2B:
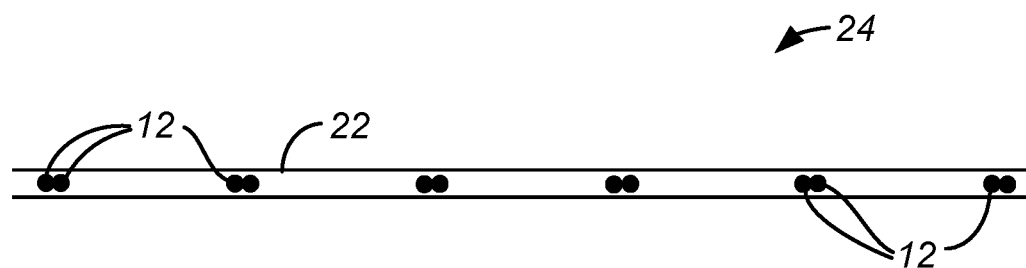
Figure 2C:
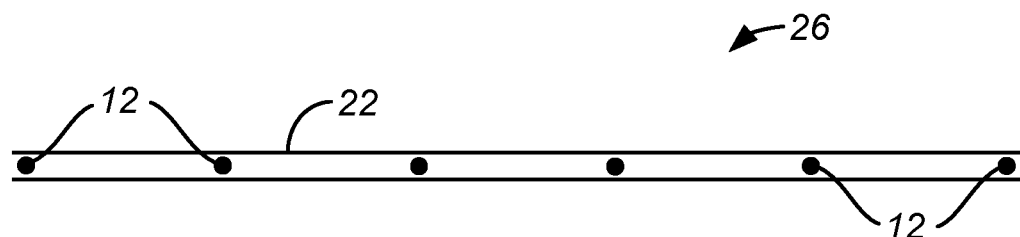

Referring now to FIGS. 2A-2C, the tethered constructs of the present invention may rely on tubular or sleeve-like structures for containing the individual or clustered radiopaque elements 12. For example, a tethered construct 20 may include a sleeve or tube 22 having an interior passage or lumen 24 which can receive the individual or clustered radiopaque elements 12. Referring specifically to FIG. 2A, the radiopaque elements 12 may be arranged as triplet four groups. As shown in FIG. 2B, there may be six paired radiopaque elements 12. Or as shown in FIG. 2C, there may be six individual radiopaque elements 12. In all cases, the radiopaque elements 12 may be immobilized within the tube or sleeve 22 using adhesives, clips, sutures, heat welding, or the like. The tubes, the sleeves themselves may be a fabric, polymer membrane, a thin walled plastic tube or like.

Figure 3A:
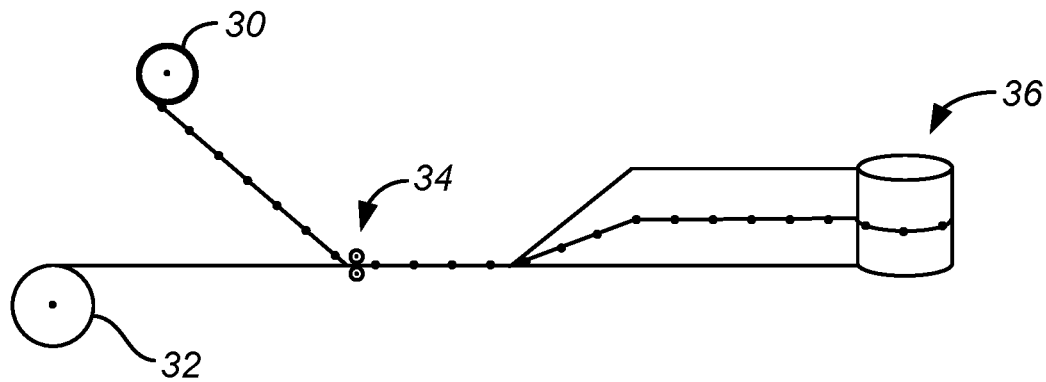
FIGS. 3A and 3B illustrate different techniques for fabricating surgical articles according to methods of the present invention.
Figure 3B:
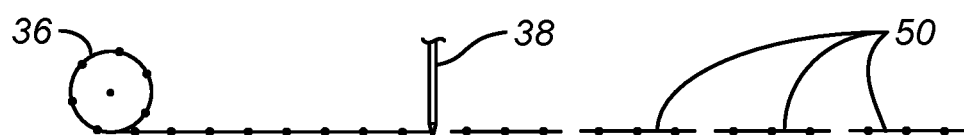

Referring now to FIGS. 3A and 3B, any of the tethered constructs described above may be secured to an absorbent fabric material as illustrated. For example, as shown in FIG. 3A, the absorbent material may be provided on a roll 30 while the tethered construct may be provided on a roll 32 where the absorbent material and tethered constructs are drawn from the rolls and passed through a pair of opposed rollers 34 which may, for example, apply heat in order to seal the tethered construct onto the absorbent fabric material. After sealing, the fabric material having the attached covered construct may then be taken up on a roll 36 which may then be further processed in order to produce individual surgical articles.

As shown in FIG. 3B, the fabric material having attached tethered constructs from roll 36 my be further processed into individual surgical articles, such as surgical sponges 50, by cutting the fabric material into desired lengths and configurations using a blade 38 or other cutting apparatus, such as laser cutting. Subsequently the individual pieces of material may be further folded or processed to convert those sections of fabric to a desired final form.

Figure 4:
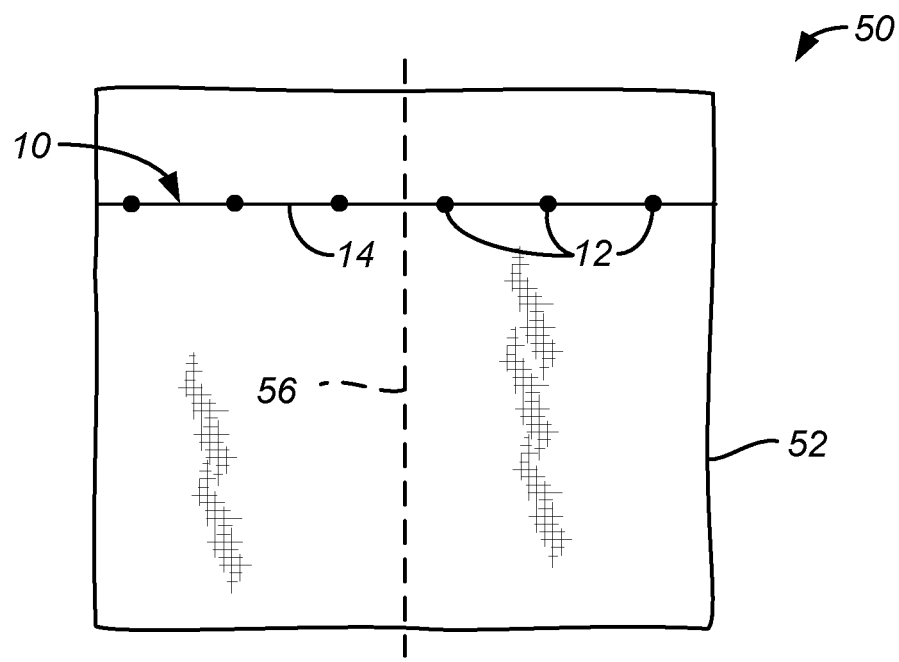
FIG. 4 illustrates a first exemplary surgical article comprising a sheet of an absorbent fabric material having a tethered construct including a plurality of discrete radiopaque elements attached thereto.

Referring now to FIG. 4, a first exemplary surgical article 50 comprises an absorbent fabric material 52, typically in the form of a square of gauze or similar surgical sponge material. The tethered construct 10 previously described may be secured to the absorbent fabric material 52, typically as shown in FIG. 3A prior to folding, so that the tethered construct 10 lies along a distribution line which crosses a fold line 56 which is typically at the center of the sponge.

As show in FIG. 5, the absorbent fabric material 52 may be folded about the fold line 56 to draw opposed halves of the distribution line of the construct 10 together in order to align individual radiopaque elements 12. The individual radiopaque elements 12 may be aligned so that they are stacked or superimposed on each other so that they each contribute to a radiopaque artifact 12'.

As shown in FIG. 6A, stacking of the individual radiopaque elements 12 will produce a greater radiopacity than the elements would without stacking. Alternatively, as shown in FIG. 6B, the individual radiopaque elements 12 may be interspersed after the absorptive fabric material 52 is folded so that the six individual radiopaque artifacts 12" so that the image shows twice as many image artifacts over each individual length (i.e., six image artifacts are visible over ½ of the original width of the absorptive fabric material 52.

Figure 7:
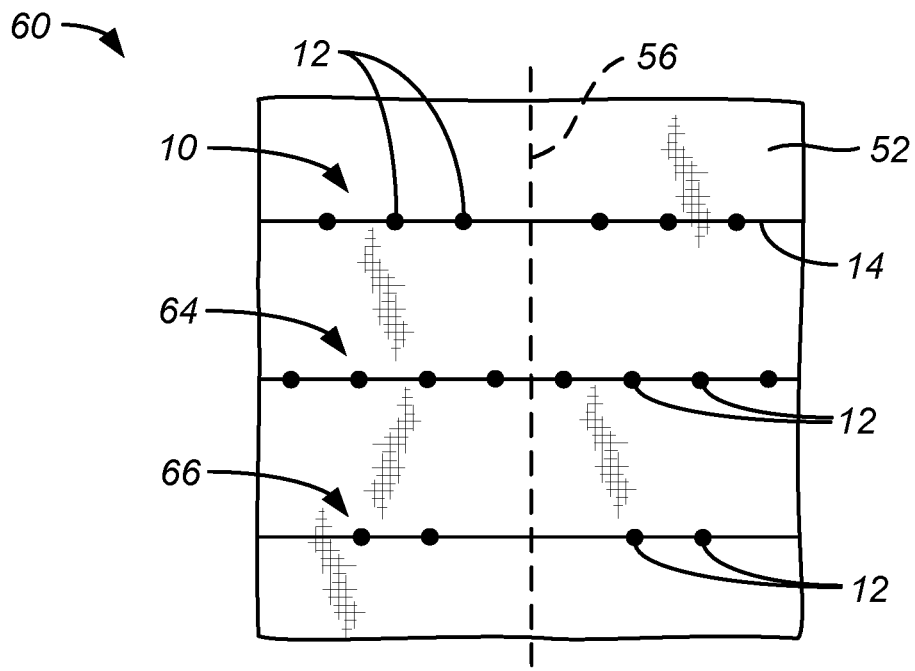
FIG. 7 illustrates a second embodiment of a surgical article constructed in accordance with the principles of the present invention having three distribution lines including radiopaque elements where each distribution line has a different spacing pattern for the individual discrete radiopaque elements.

Referring to FIG. 7, a second exemplary surgical article 16 comprises three individual tethered constructs attached to the absorptive fabric material 52. A first construct may be the same as any of the previously described constructs, for example, being construct 10. A second tethered construct 64 may include a total of eight radiopaque elements 12 along its distribution line. A third tethered construct 66 may include only four radiopaque elements 12 along its length.

Figure 8:
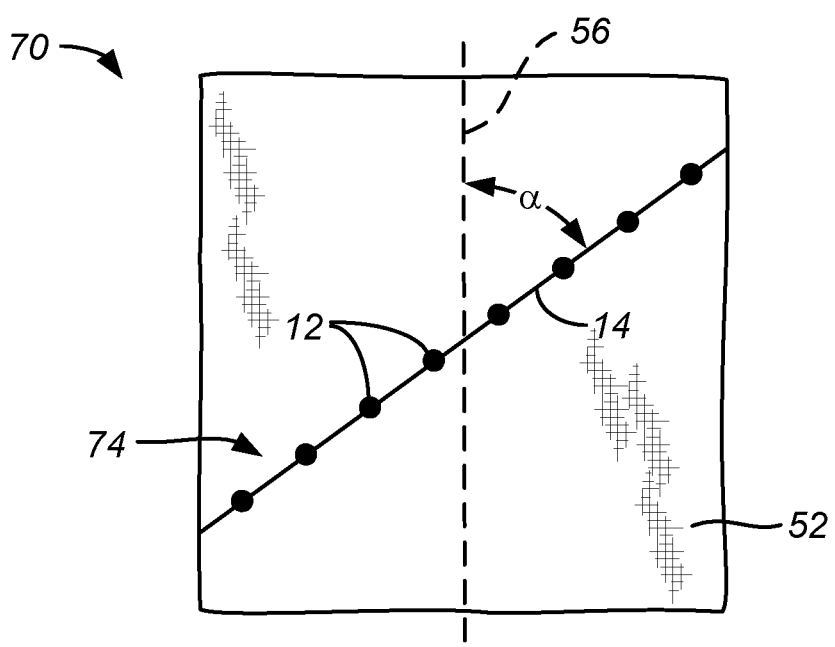
FIG. 8 illustrates a third embodiment of the surgical article of the present invention having a single distribution line including the plurality of radiopaque elements inclined at an acute angle relative to the fold line.

Referring now to FIG. 8, a third exemplary surgical article 70 includes a tethered construct 74 which includes a total of eight radiopaque elements 12 along its distribution line. The distribution line which lies along filament 14 is inclined at an angle alpha α relative to fold line 56. In this way, when the absorptive half brick material is folded along line 56, the resulting image artifact will be in a V-shape when viewed under fluoroscopy or x-ray.

Figure 9:
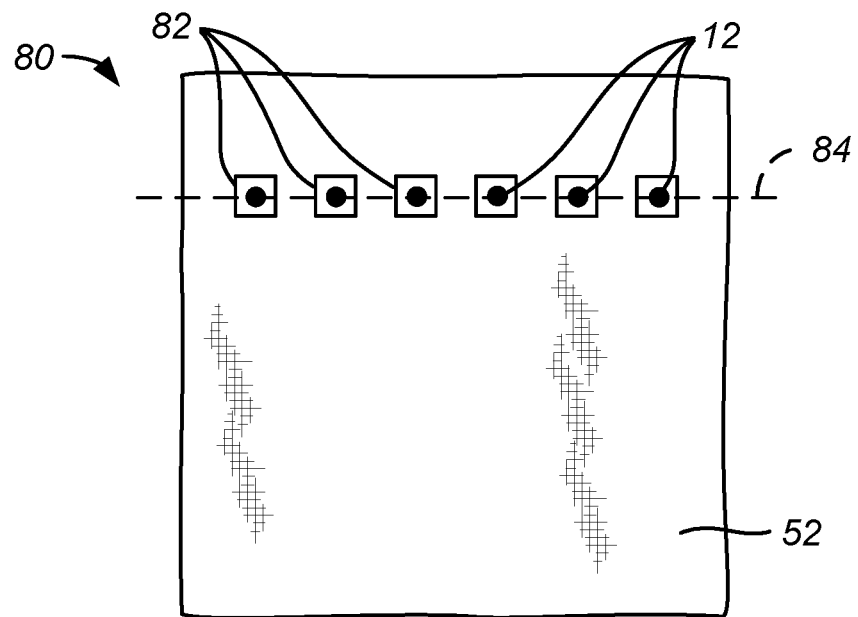
FIG. 9 illustrates a fourth embodiment of a surgical article constructed in accordance with the principles of the present invention having a plurality of discrete radiopaque elements disposed in individual pockets aligned along a single distribution line.

Referring now to FIG. 9, a fourth exemplary surgical article 80 includes a plurality of both individual radiopaque elements 12 disposed in individual pockets 82 which are distributed along a distribution line 84. The pockets will be sealed in order to contain the radiopaque elements on the absorptive fabric material 82. The pockets 82 may be part of the fabric material, e.g., being woven or sewn into the fabric. Alternatively, the pockets may be separately heat sealed or otherwise adhere to a surface of the absorptive fabric material 52.

Figure 10:
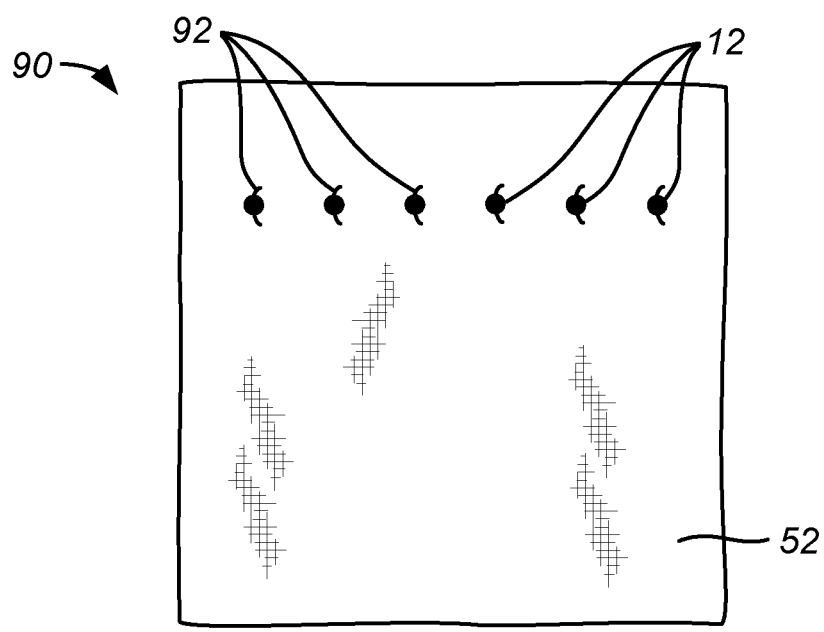
FIG. 10 illustrates a fifth embodiment of a surgical article constructed in accordance with the principles of the present invention having a plurality of discrete radiopaque elements sutured along a distribution line to a sheet of absorbent fabric material.

Referring now to FIG. 10, a fifth exemplary embodiment of a surgical article constructed in accordance with the principles of the present invention comprises a plurality of individual radiopaque articles 12 which are sutured using suture hoops 92 to the absorptive fabric material. Radiopaque articles 12 having holes or passages through of the type which may be placed over a filament can be used for the suturing embodiments.

In alternative embodiments, the ribbon or other elongated marker substrate will typically comprise a custom compounded polymer having characteristics which include: (1) radiopaque elements, components or materials of a nature and amount that can be visualized under fluoroscopy when present on the sponge as a thin film; (2) sufficient flexibility following extrusion, processing, and conversion to a final format to bend along with the sponge material onto which it is affixed so as to not inhibit the intended function or feel of the sponge; (3) ability to be adhered to the surface of gauze surgical sponge material e.g. by heat pressing so that the material attaches to the sponge material, in the case of being sewn to the sponge material and/or by stitching through and hold that stitch; (4) ability to be formed and/or shaped, e.g. by die cutting; and (5) ability to hold a color that will contrast with both a dry sponge (white material with no blood) and wet sponge (white material with blood hence made red in color). Exemplary colors include blue and purple.

The substrate materials are typically polymer materials which are combined with radiopage additive, such as barium sulfate. The polymer materials and additives are selected to give the substrate desired characteristics in its final form. The polymer materials and additives are mixed and/or blended together and are then extruded into a film having a desired thickness. The film is then cut into desired lengths and widths and is further cut to allow portions to be removed to form regions in the substrate having a different radiopacity, typically being radio translucent when the material is cut out and removed entirely. In other embodiments, the substrate may just be formed with regions which have a lesser radiopacity or have a complete absence of radiopaque material, but usually cutting and removal will be the most efficient technique for forming the radiolucent and radio transparent regions in the body of the substrate.

Figure 11A:
FIG. 11A illustrates an alternative radiopaque marker comprising a ribbon of radiopaque material having portions which are cut-out into distinct shapes.
Figure 11B:
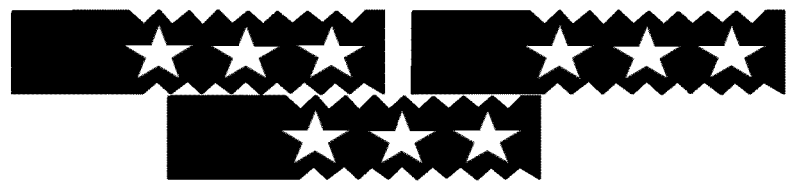
FIG. 11B illustrates the radiopaque ribbon of FIG. 11A cut into shorter segments each of which includes portions which are cut-out into distinct shapes.

In specific examples, the radiolucent and transparent regions will have two-dimensional shapes made by removing material from the film. This may be done by running the film through a customized rotary die cutter which cuts the desired shaping in the film in a relatively continuous fashion. The shaping may include both cutting and removing material along the edge and the middle of the film. Cutting along the edge may include making a saw tooth or wave like pattern. Cutting into the middle of the film may include cutting and removing material to create a distinct shape in the middle of the material. By removing material from the middle of the film that shape will be recognizable under x-ray as that area will not include radiopaque materials. Such distinct shape may be a common geometric or other shape such as a circle, triangle or star. FIG. 11A shows an example of shaping the film by cutting and removing material from both the end and middle of the film. The edge regions are cut as a saw tooth pattern while the middle cut-out portions have a star shape. The converted film may be then applied in a continuous fashion to sponge material, or alternatively the film may first may be cut into desired lengths, as shown in FIG. 11B, and then applied to the gauze or other sponge material in a non-continuous process.

The shaped film is typically affixed to the sponge material using either a sewing process or a heat press process. In the case of a sewing process, the substrate is affixed by stitching the substrate to the sponge material. This can be done in a continuous process (a long segment of substrate is affixed across sponge material that will subsequently be cut into multiple sponges) or if the substrate is cut into a desired length can be done in a non-continuous process (one or more discrete segments of substrate are attached to sponge material that will comprise one sponge).

In the case of a heat press process, the substrate is positioned on sponge material and a combination of heat and pressure are applied so as to melt the substrate (or at least the layer/portion contacting the sponge material) onto the sponge material. This can be done in a continuous process (a long segment of substrate is affixed across sponge material that will subsequently be cut into multiple sponges) or if the substrate is cut into shorter desired lengths can be done in a non-continuous process (one or more discrete segments of substrate are attached to sponge material that will comprise one sponge). In the case of a relatively continuous process, the sponge material and shaped substrate may be run through rollers (one or both being heated) and pressing against each other at a specific pressure so that the combination of heat, pressure and speed at which the materials are run through the rollers will affix the continuous substrate to the sponge material. In the case of affixing shorter discrete segments of substrate either a similar roller based approach can be used or alternatively a fixed size heat press head can be applied directly over the segment of substrate and sponge material and held at a certain pressure and temperature to affix the substrate to the sponge material. One or more discrete segments of substrate may be applied to sponge material comprising one individual sponge.

In the case of the substrate being applied in a relatively continuous process (be it via sewing or heat press where a relatively long length of shaped substrate is affixed to sponge material to be subsequently cut into multiple individual sponges), the substrate may be affixed to the sponge material in a varying location on the sponge material, so that, when that sponge material is subsequently cut and folded into individual sponges the substrate will not be folded on top of itself, thus increasing the surface area of the substrate exposed to be seen under x-ray. If the substrate is applied in a constant location on the uncut sponge material, when cut and folded the substrate may be folded on top of itself and not provide as much exposed surface area to be seen. Examples of varying positions include affixing the substrate to uncut sponge material in an "S" or "V" like pattern.

Figure 12A:
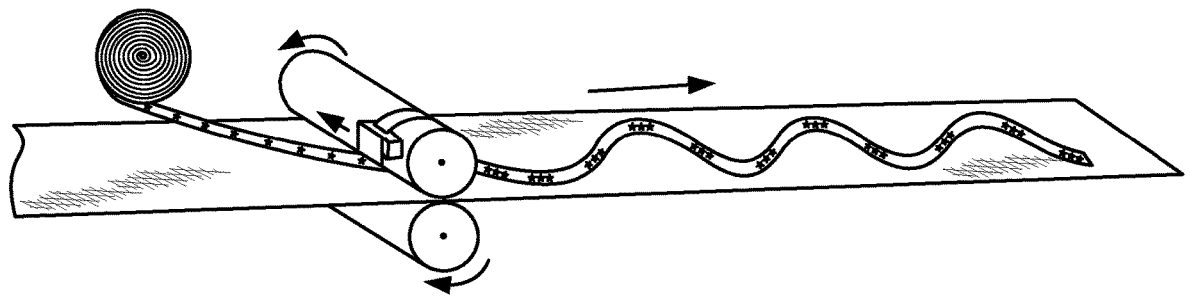
FIG. 12A illustrates a method for adhering a continuous length of radiopaque ribbon identical or similar to that shown in FIG. 11A in a serpentine pattern to a continuous length of surgical gauze prior to cutting and formation into surgical sponges.
Figure 12B:
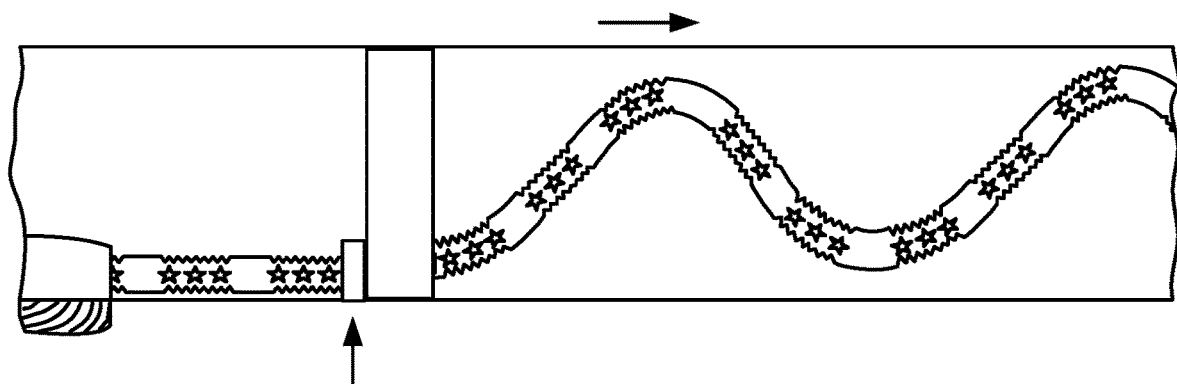
FIG. 12B illustrates the method and system of FIG. 12A shown from a top view.

FIG. 12A is aside view of a continuous sheet of gauze sponge material and a continuous length of a substrate ribbon being applied and passed through opposed heated rollers which affixes the substrate in a continuous process at varying positions in an "S" pattern. FIG. 12B is a top view of the sponge material and substrate of FIG. 12A being run through heated rollers and affixing substrate in a continuous pattern at varying positions in an "S" pattern.

Figure 13:
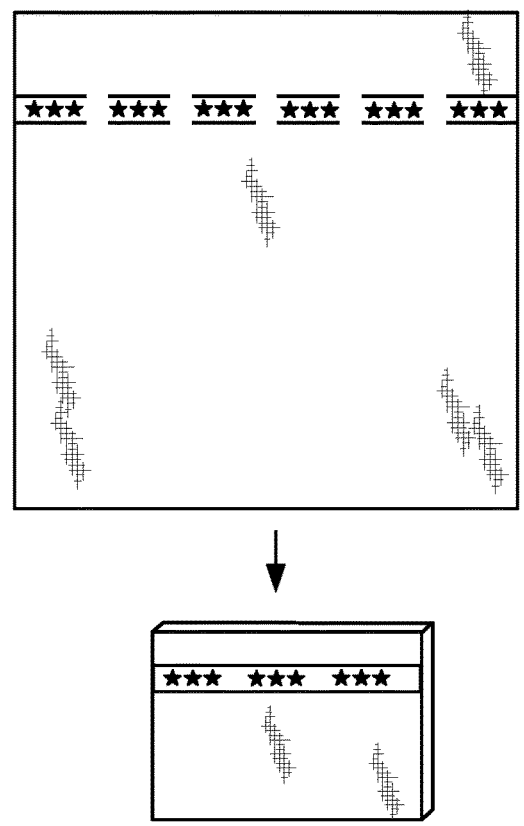
FIG. 13 shows a surgical sponge with a straight segment of patterned, radiopaque ribbon on a surface there of before and after folding.
Figure 14:
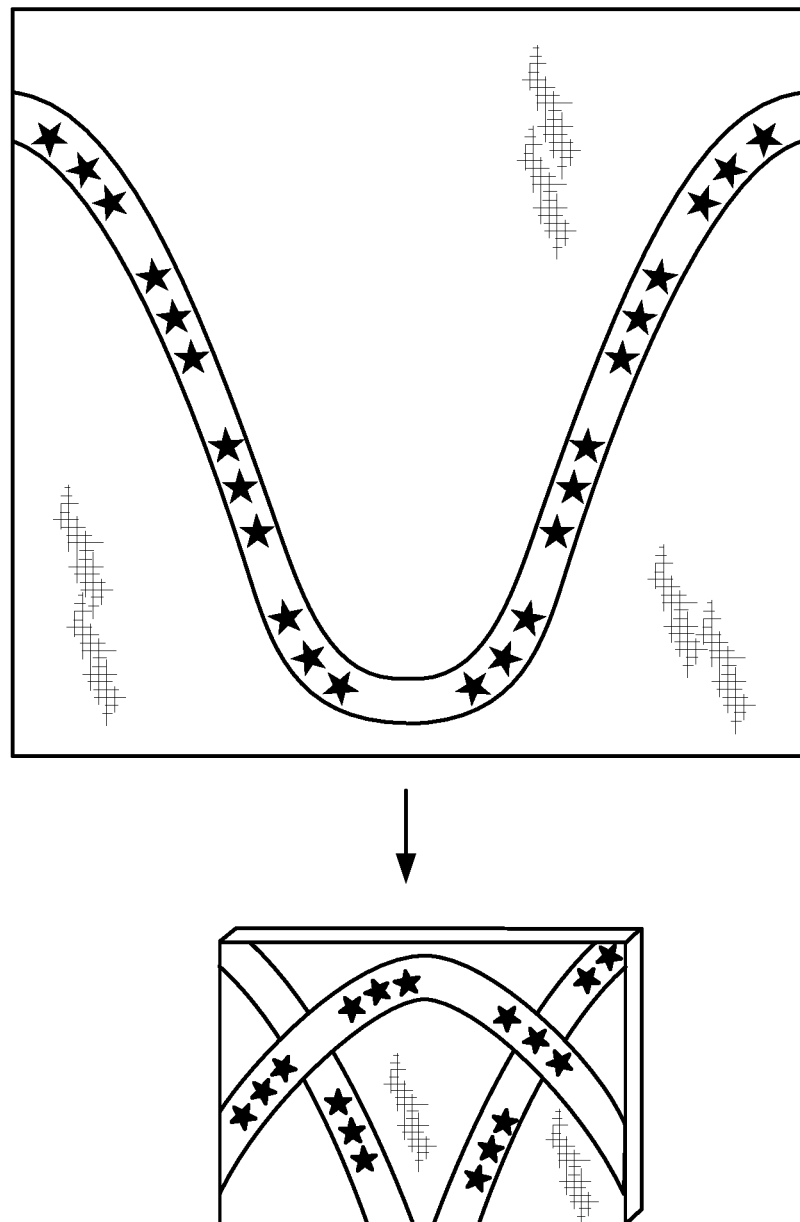
FIG. 14 shows a surgical sponge with a serpentine segment of patterned, radiopaque ribbon on a surface there of before and after folding.

Comparing FIG. 13 with FIG. 14 shows the benefits of varying the position of the ribbon relative to substrate when affixing to a single layer of sponge material that is later folded multiple times to form a final sponge. In FIG. 13, the substrate is applied in a fixed position. When folded the substrate is folded upon itself so there is relatively little exposed surface area of substrate. In FIG. 14, in contrast, the position of the substrate is varied into an "S" shape so as to result in more exposed surface area of substrate when folded into final folded sponge.

What is claimed is:

1. A surgical article comprising
a sheet of absorbent material; and
at least one elongate ribbon comprising a radiopaque material attached to the sheet of absorbent material, said ribbon having portions cut out from the ribbon and portion that remain, wherein the cut out portions are radiolucent and the portions that remain are radiopaque;
wherein the portions which are radiopaque and the portions which are radiolucent together form a pattern of multiple image artifacts distributed along a length of the ribbon and across a surface of the sheet of absorbent material.

2. The surgical article of claim 1, wherein the elongate ribbon is attached to the sheet of absorbent material by heat pressing with rollers.

3. The surgical article of claim 1, wherein the elongate ribbon is attached to the sheet of absorbent material in a serpentine pattern.

4. The surgical article of claim 1, wherein the ribbon comprises a film formed from a polymer combined with radiopaque additive.

5. The surgical article of claim 4, wherein the film has a length, a width, a thickness, and two edges.

6. The surgical article of claim 5, wherein the cut outs have a repeating pattern.

7. The surgical article of claim 6, wherein the repeating pattern comprises a circle, a triangle or a star.

8. The surgical article of claim 5, wherein at least some of the cut outs are formed in an edge.

9. The surgical article of claim 8, wherein cut out along the edge comprise a saw tooth pattern or a wave-like pattern.

10. The surgical article of claim 1, wherein the cut outs are filled with a material having a differing radiopacity.

11. The surgical article of claim 1, wherein the cut outs are unfilled.

12. The surgical article of claim 4, wherein the polymer and radiopaque additives are mixed and/or blended together and extruded into a film where the film is then cut into lengths and widths and is further cut to form cut out regions.

* * * * *